(12) United States Patent
Xu et al.

(10) Patent No.: US 12,012,580 B1
(45) Date of Patent: Jun. 18, 2024

(54) ASSAY SYSTEM AND METHOD FOR ACCURATELY ANALYZING NON-CONTACT TOXICITY OF CANDIDATE COMPOUNDS ON INSECTS

(71) Applicants: Peng Xu, Reno, NV (US); Li Cheng, Reno, NV (US)

(72) Inventors: Peng Xu, Reno, NV (US); Li Cheng, Reno, NV (US)

( * ) Notice: Subject to any disclaimer, the term of this patent is extended or adjusted under 35 U.S.C. 154(b) by 26 days.

(21) Appl. No.: 17/327,249

(22) Filed: May 21, 2021

Related U.S. Application Data

(63) Continuation-in-part of application No. 16/557,479, filed on Aug. 30, 2019, now Pat. No. 11,097,643.

(51) Int. Cl.
| | |
|---|---|
| *C12M 1/00* | (2006.01) |
| *A01M 1/20* | (2006.01) |
| *B01L 3/00* | (2006.01) |
| *C12M 1/22* | (2006.01) |
| *C12M 1/26* | (2006.01) |
| *C12M 3/06* | (2006.01) |
| *G01N 21/84* | (2006.01) |

(52) U.S. Cl.
CPC .............. *C12M 23/38* (2013.01); *A01M 1/20* (2013.01); *B01L 3/508* (2013.01); *B01L 3/561* (2013.01); *C12M 23/10* (2013.01); *C12M 23/16* (2013.01); *C12M 23/22* (2013.01); *C12M 33/04* (2013.01); *C12M 33/14* (2013.01); *G01N 21/84* (2013.01); *A01M 2200/01* (2013.01); *B01L 2300/126* (2013.01); *B01L 2400/043* (2013.01)

(58) Field of Classification Search
None
See application file for complete search history.

(56) References Cited

U.S. PATENT DOCUMENTS

| | | | | |
|---|---|---|---|---|
| 2004/0223998 | A1* | 11/2004 | Iyer | A01N 65/06 424/405 |
| 2017/0335868 | A1* | 11/2017 | Coronado | B01L 9/52 |

FOREIGN PATENT DOCUMENTS

| | | | |
|---|---|---|---|
| CN | 207767375 U | * | 8/2018 |
| JP | H1189561 A | * | 4/1999 |

OTHER PUBLICATIONS

Translation of CN207767375U, Lai, Rong-hong, Aug. 28, 2018 (Year: 2018).*

* cited by examiner

*Primary Examiner* — Maris R Kessel
*Assistant Examiner* — Henry H Nguyen
(74) *Attorney, Agent, or Firm* — Richard Eldredge; Eldredge Law Firm

(57) ABSTRACT

An analyzing system for pesticide effectiveness includes a transparent container having an interior area, the transparent container having a port extending through a wall of the transparent container; a bracket positioned within the interior are of the transparent container; a dish having a dish interior area configured to hold a test insect, the dish to be supported by the bracket within the transparent container; an injection device to inject a test liquid into the interior area of the transparent container through the port; the dish is to hold the test insect a distance from an injected test liquid; and the transparent container provides for visual observations of an effect of the test liquid on the test insect.

3 Claims, 1 Drawing Sheet

ASSAY SYSTEM AND METHOD FOR ACCURATELY ANALYZING NON-CONTACT TOXICITY OF CANDIDATE COMPOUNDS ON INSECTS

BACKGROUND

1. Field of the Invention

The present invention relates generally to testing systems, and more specifically, to an assay system for testing vapors on insects.

2. Description of Related Art

Pesticides are well known in the art and provide a means to control insects and pests, such as on plant matter. Conventional systems use pesticides which rely on either contact toxicity or non-contact toxicity. Contact toxicity requires that the insect contact the surface of the applied pesticide, wherein their skin then picks up the compound, which then takes effect on the inset. Non-contact toxicity relies on vapor toxicity and possible particles toxicity, in which the pesticide acts on the insect without contact. Most non-contact pesticides are made into liquid and emit vapor, and some diffuse airborne particles into the air. In conventional testing systems, contact of the pesticide to the insect is provided, which then will tell a mixed toxicity of both contact toxicity and non-contact assay as insects contact with the coating area of the bottle, but also exposed to the unseen vapor or particles. We cannot eliminate the potential effect of non-contact toxicity, as the role of vaper and particles was neglected.

Therefore, it is necessary to have a precise assay specifically for non-contact toxicity test to isolate it from contact toxicity of the candidate compound, especially, for these pesticides which mostly show toxicity rely on vaper or particles.

A more objective and effective assay will facilitate the discovery and development of novel active ingredients with inherent spatial repellent properties. The present design seeks to specifically build an insect non-contact toxicity (INCT) assay which is efficient to show potency of toxicity of candidate compounds with volatile constituents graphically and facilitate accurate quantitative analysis.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
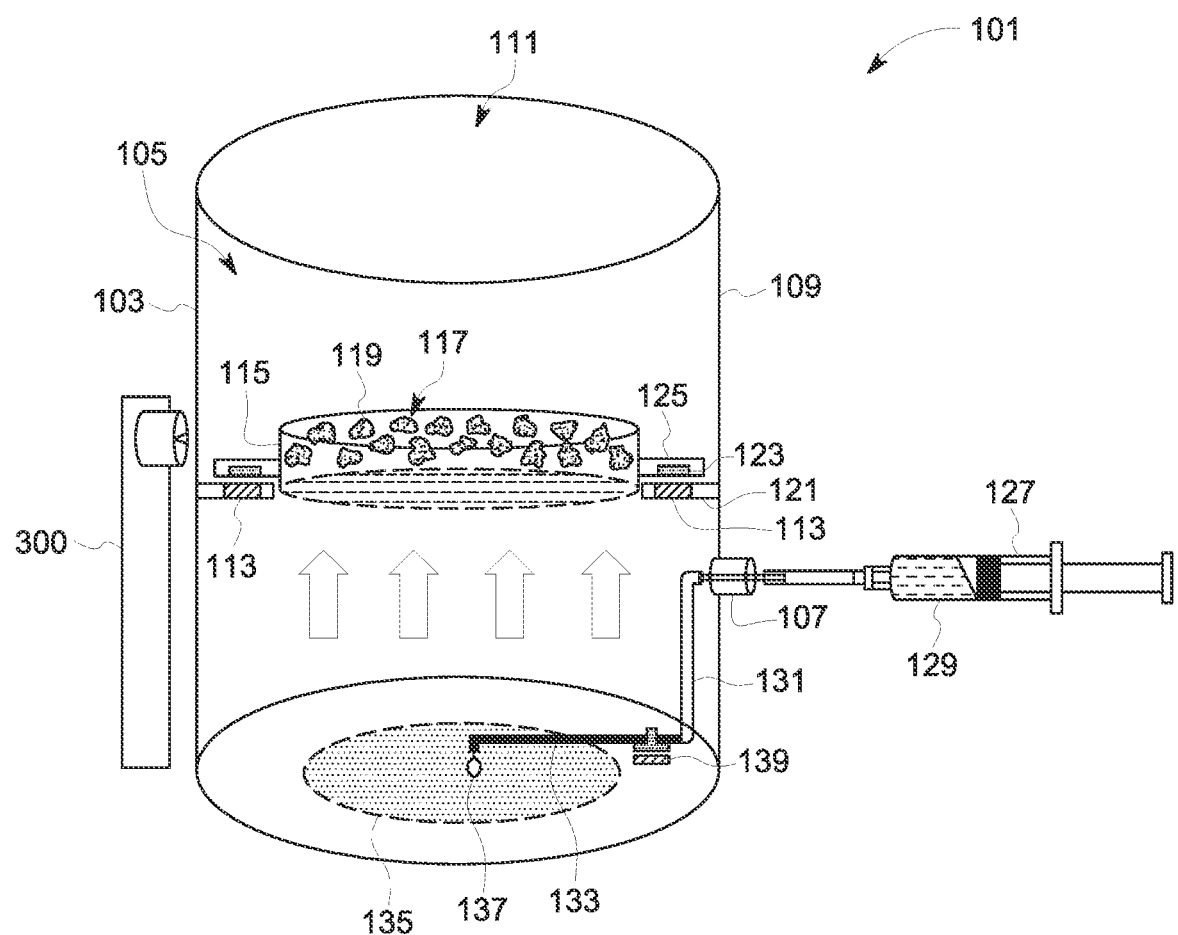
FIG. 1 is a front view of an analyzing system in accordance with a preferred embodiment of the present application.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional pesticide testing systems. Specifically, the present invention provides for a simple analyzing system and method that tests the effectiveness of non-contact pesticides. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIG. 1 depicts a front view of an analyzing system in accordance with a preferred embodiment of the present application. It will be appreciated that system 101 overcomes one or more of the above-listed problems commonly associated with conventional analyzing systems.

In the contemplated embodiment, system 101 includes a transparent container 103 having an interior area 105 and a port 107 extending through a wall 109 of the transparent container. It should be appreciated that the transparent container is preferably cylindrical in shape, however, the teachings of the present invention may be adapted for configuration with various shapes. It should further be appreciated, that in the preferred embodiment, the transparent container 103 includes a sealable lid, however, it is further contemplated that the top end 111 may be permanently closed, or open based on the testing desires of the user. It should be appreciated that in the preferred embodiment, the container is sealed when in use to precisely test the vapors.

System 101 further includes a bracket 113 positioned within the interior are of the transparent container, the bracket configured to support a dish 115 having a dish interior area 117, wherein the dish is configured to hold a test insect 119. As shown, it is contemplated that the bracket may include two or more sides and include a first magnet 121 configured to secure to a second magnet 123 within a dish holder 125.

In some embodiments, the dish will may be covered and include a wire mesh to allow particles to impact the insects.

An injection device 127 is provided to inject a test liquid 129 into the interior area of the transparent container through the port. As shown, the injection device 127 in the preferred embodiment is a syringe, however, it should be appreciated that modifications could be made.

It should be appreciated that the exact means and location of the test liquid may be varied, however, in the preferred embodiment, a piece of tubing 131 directs the liquid to a perfusion tube 133, which further directs the test liquid to a filter paper 135 positioned at the bottom of the container. The injected liquid 137 will either emit particles or fumes that do not come into direct contact with the insects, thereby allowing for testability of non-contact effects of the liquid.

As shown, in some embodiments, the perfusion tube is held in place via a magnetic holder 139. However, it is contemplated that other holders may be used.

It should be appreciated that one of the unique features believed characteristic of the present application is the configuration of the system that allows for easy testing of non-contact pesticides.

The system may include a digital recording camera 300 on the wall at a close level of the dish. The user will then click the recording software in a computer to focus on insects and be ready to record their performance. Count the numbers of insects are killed under this circumstance and calculate statistical mortality caused by different of concentrations to generate Lethal Concentration 50 to determine the non-contact toxicity of candidate compounds. Meanwhile, list the time point of each individual insect's death from the video and the average value of killing time are collected.

Figure 2:
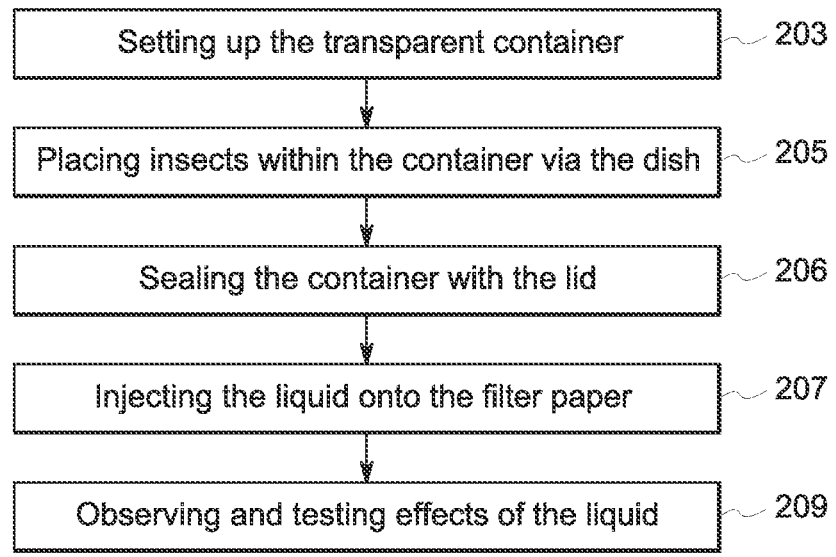
FIG. 2 is a flowchart of a method of use of the system of FIG. 1.

In FIG. 2, a flowchart 201 depicts a method of use of system 101. During use, the system will be set up, as shown with box 203. The user will place the test insects within the transparent container via the dish and seal the transparent container, as shown with boxes 205, 206. The user will then proceed to inject the test liquid into the container and onto the filter paper, as shown with box 207. The user can then determine the effects of the liquid such via non-contact, as shown with box 209.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is a:

1. An analyzing system for pesticide effectiveness, comprising:
    a transparent container having an interior area, the transparent container having:
        a port extending through a wall of the transparent container;
        a bracket positioned within the interior area of the transparent container;
        a dish having a dish interior area configured to hold a test insect, the dish to be supported by the bracket within the transparent container;
        an injection device configured to inject an injected test liquid into the interior area of the transparent container through the port;
    a filter paper positioned near a bottom of the transparent container, the filter paper to receive the injected test liquid;
    a piece of tubing extending from the port and configured to transport the test liquid;
    a perfusion tube attached to an end of the piece of tubing and configured to deliver the test liquid to the filter paper; and
    a magnetic holder attached to the perfusion tube and securing the perfusion tube at a desired location;
    wherein the dish is configured to hold the test insect a distance from the injected test liquid; and
    wherein the transparent container provides for visual observations of an effect of the test liquid on the test insect.

2. The system of claim 1, wherein the bracket includes a first magnet and the dish includes a second magnet, wherein the first and second magnets engage to hold the dish within the interior area.

3. The system of claim 1, wherein the dish is positioned above the injected test liquid.

* * * * *